US012564359B2

(12) United States Patent
Quigg et al.

(10) Patent No.: US 12,564,359 B2
(45) Date of Patent: Mar. 3, 2026

(54) SYSTEMS, METHODS, AND COMPUTER READABLE MEDIUMS FOR PERFORMING DYNAMIC POSITRON EMISSION TOMOGRAPHY

(71) Applicant: University of Virginia Patent Foundation, Charlottesville, VA (US)

(72) Inventors: Mark S. Quigg, Charlottesville, VA (US); Bijoy Kundu, Charlottesville, VA (US); James C. Massey, Charlottesville, VA (US); Vikram Seshadri, Richmond, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 238 days.

(21) Appl. No.: 18/267,272

(22) PCT Filed: Dec. 14, 2021

(86) PCT No.: PCT/US2021/063313
§ 371 (c)(1),
(2) Date: Jun. 14, 2023

(87) PCT Pub. No.: WO2022/132772
PCT Pub. Date: Jun. 23, 2022

(65) Prior Publication Data
US 2024/0057950 A1      Feb. 22, 2024

Related U.S. Application Data

(60) Provisional application No. 63/125,144, filed on Dec. 14, 2020.

(51) Int. Cl.
*A61B 6/00*           (2024.01)
*A61B 5/055*          (2006.01)
(Continued)

(52) U.S. Cl.
CPC .............. *A61B 6/037* (2013.01); *A61B 5/055* (2013.01); *A61B 6/4417* (2013.01); *A61B 6/501* (2013.01);
(Continued)

(58) Field of Classification Search
None
See application file for complete search history.

(56) References Cited

U.S. PATENT DOCUMENTS

2008/0287772 A1* 11/2008 Declerck ................ A61B 6/037
                                                              382/131
2011/0299747 A1* 12/2011 Solf ........................ G16H 30/20
                                                              382/128

(Continued)

OTHER PUBLICATIONS

Notification of Transmittal of the International Search Report and the Written Opinion of the International Searching Authority, or the Declaration for International Application No. PCT/US2021/063313 (Mar. 1, 2022).

(Continued)

*Primary Examiner* — Hoon K Song
(74) *Attorney, Agent, or Firm* — Jenkins, Taylor & Hunt, P.A.

(57) ABSTRACT

A method for performing dynamic positron emission tomography (PET) is disclosed. The method includes collecting volumetric radioactive measurement data associated with an administered radioactive tracer present in a target site of a subject over multiple scanning intervals, capturing a magnetic resonance image of the target site, and performing a motion correction process to the volumetric radioactive measurement data to produce motion corrected PET data. The method further includes co-registering the magnetic resonance image and motion corrected data to generate a co-registered dynamic PET volume, and applying a model corrected input function (MCIF) to the co-registered
(Continued)

dynamic PET volume to calibrate an uptake amount of the radioactive tracer in the target site.

20 Claims, 10 Drawing Sheets

(51) Int. Cl.
A61B 6/03          (2006.01)
A61B 6/50          (2024.01)
A61B 6/58          (2024.01)
G06T 7/30          (2017.01)

(52) U.S. Cl.
CPC .......... A61B 6/5247 (2013.01); A61B 6/5264 (2013.01); A61B 6/582 (2013.01); G06T 7/30 (2017.01)

(56)                     References Cited

U.S. PATENT DOCUMENTS

2014/0296698 A1*  10/2014  Bauer  .................. A61B 6/5264
                                                     324/322
2020/0261032 A1     8/2020  Li et al.

OTHER PUBLICATIONS

Notification of Transmittal of the International Preliminary Report on Patentability for International Application No. PCT/US2021/063313 (Jun. 29, 2023).

* cited by examiner

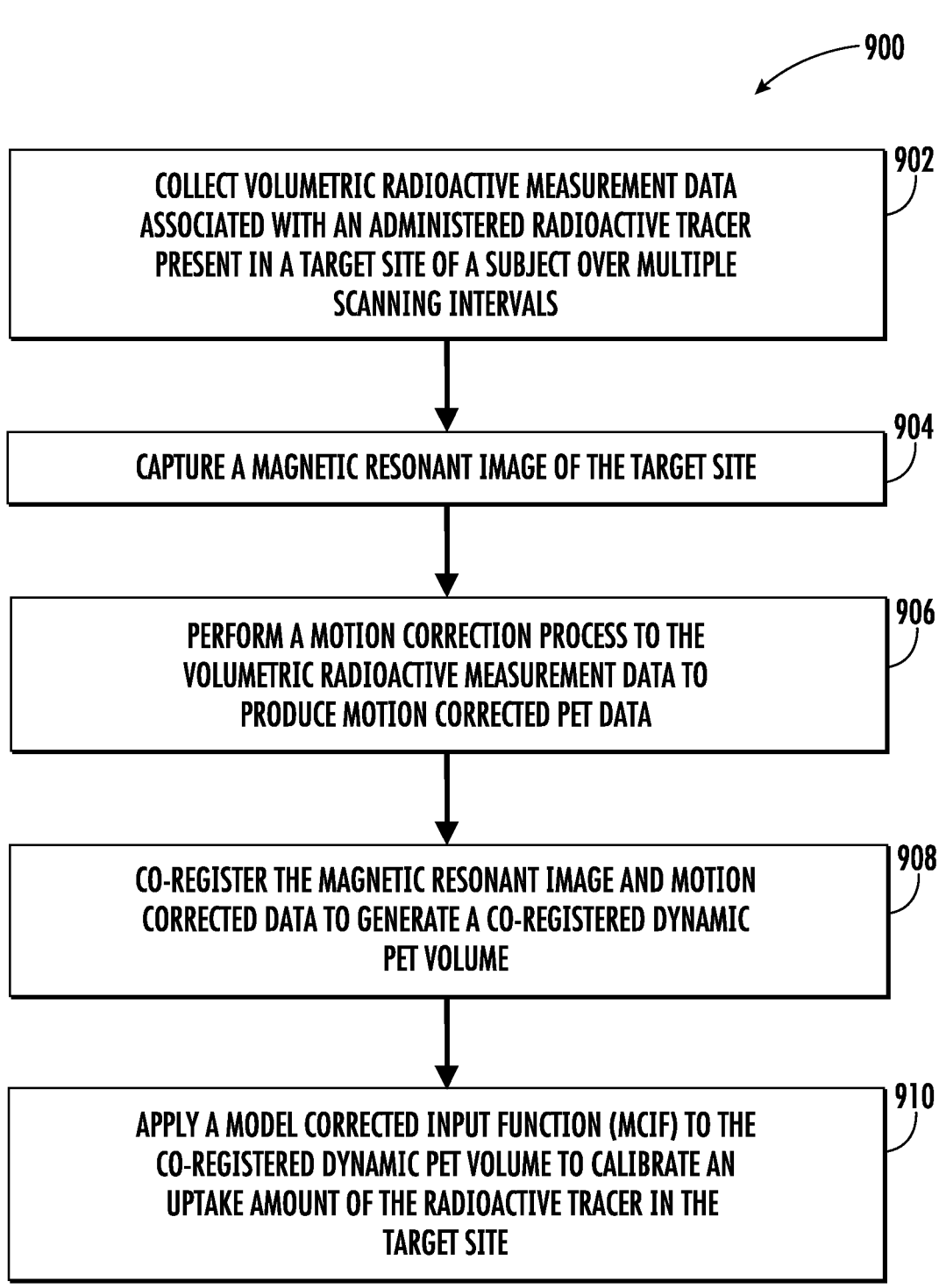

900

COLLECT VOLUMETRIC RADIOACTIVE MEASUREMENT DATA ASSOCIATED WITH AN ADMINISTERED RADIOACTIVE TRACER PRESENT IN A TARGET SITE OF A SUBJECT OVER MULTIPLE SCANNING INTERVALS ⟋902

CAPTURE A MAGNETIC RESONANT IMAGE OF THE TARGET SITE ⟋904

PERFORM A MOTION CORRECTION PROCESS TO THE VOLUMETRIC RADIOACTIVE MEASUREMENT DATA TO PRODUCE MOTION CORRECTED PET DATA ⟋906

CO-REGISTER THE MAGNETIC RESONANT IMAGE AND MOTION CORRECTED DATA TO GENERATE A CO-REGISTERED DYNAMIC PET VOLUME ⟋908

APPLY A MODEL CORRECTED INPUT FUNCTION (MCIF) TO THE CO-REGISTERED DYNAMIC PET VOLUME TO CALIBRATE AN UPTAKE AMOUNT OF THE RADIOACTIVE TRACER IN THE TARGET SITE ⟋910

FIG. 9

SYSTEMS, METHODS, AND COMPUTER READABLE MEDIUMS FOR PERFORMING DYNAMIC POSITRON EMISSION TOMOGRAPHY

CROSS REFERENCE TO RELATED APPLICATIONS

This application is a national stage filing of PCT International Patent Application No. PCT/US2021/063313, filed Dec. 14, 2021, which claims the benefit of U.S. Provisional Patent Application Ser. No. 63/125,144, filed Dec. 14, 2020; the disclosure of which is incorporated herein by reference in its entirety.

TECHNICAL FIELD

The subject matter described herein relates to neurologic disorder analysis methods and FDG-PET procedures. More particularly, the subject matter described herein relates to methods, systems, and computer readable media for performing dynamic positron emission tomography (PET).

BACKGROUND

In the United States and other industrialized countries, where various antiepileptic drugs are readily accessible, many patients continue to have seizures that are not adequately controlled by available medications. Best-practice guidelines recommend that patients with medically intractable focal epilepsy undergo evaluation for epilepsy surgery to remove the seizure focus. Identifying (or "localizing") the seizure focus can be straightforward when a lesion is identified via magnetic resonance imaging (MRI) and other information that is concordant with that finding. However, many patients with seizures identified by focal changes on an electroencephalogram (EEG) do not have a lesion indicated on MRI images. In that subset, subsequent surgery, usually enabled by invasive monitoring techniques, has a less favorable outcome in cryptogenic patients as compared to those patients with focal lesions present on imaging. Thus, enhancing the ability to locate seizure foci in nonlesional focal epilepsy patients is critical for identifying surgical targets.

Fluorodeoxyglucose (FDG)-positron emission tomography (PET) (FDG-PET) forms one component of the noninvasive stage of presurgical localization because it measures neuronal metabolism rather than anatomy, as is done by MRI, or electrical activity as is done by EEG. When measured between seizures, metabolically hypoactive regions revealed by decreased glucose uptake correspond to seizure foci.

Current PET procedures have limitations. For example, in a study of the value of presurgical tests, identification of seizure foci with PET predicted one year seizure-remission in a longitudinal study with clinically useful odds ratios, but odds ratios were lower than other localizing methods such as ictal SPECT, the presence of pre-operative auras, or concordance among pre-surgical procedures. In another example, when focal hypometabolism demonstrated on PET is ipsilateral to the side of the presumed seizure focus, seizure-free outcomes in those with otherwise unknown foci are similar to those in patients with lesional temporal lobe epilepsy. The role of PET becomes especially important because many patients in recent surgical series lack clear MRI lesions, and the identification of a metabolic abnormality closely correlated with other evaluations of the surgical focus is associated with better postoperative seizure control. When focal PET hypometabolism is present, but the MRI is normal, surgical outcome is equivalent to those patients with clear MRI lesions. In those patients with normal MRI and discordant noninvasive data, PET aids in triage. For example, a majority of patients with normal MRI and discordant data had focal PET abnormalities. Of those patients, many went on to have invasive monitoring or epilepsy surgery guided by standard PET.

Accordingly, there exists a need for improved methods and systems for performing dynamic positron emission tomography.

SUMMARY

A method for performing dynamic positron emission tomography (PET) includes collecting volumetric radioactive measurement data associated with an administered radioactive tracer present in a target site of a subject over multiple scanning intervals, capturing a magnetic resonance image of the target site, and performing a motion correction process to the volumetric radioactive measurement data to produce motion corrected PET data. The method further includes co-registering the magnetic resonance image and motion corrected data to generate a co-registered dynamic PET volume, and applying a model corrected input function (MCIF) to the co-registered dynamic PET volume to calibrate an uptake amount of the radioactive tracer in the target site.

According to another aspect of the method described herein, continuously collecting a plurality of volumetric radioactive measurements at multiple scanning intervals over a predefined time period.

According to another aspect of the method described herein, prior to the collecting step, the subject is injected with the radioactive tracer.

According to another aspect of the method described herein, the volumetric radioactive measurement data indicates a changing of concentrations of the radioactive tracer per each of the multiple scanning intervals.

According to another aspect of the method described herein, the MCIF is determined and applied automatically via an artificial neural network (ANN).

According to another aspect of the method described herein, the MCIF is used to generate objective parametric PET maps of the target site.

According to another aspect of the method described herein, a plurality of blood time activity curves generated from a plurality of frames of the co-registered dynamic PET volume is used to derive the MCIF.

According to another aspect of the subject matter described herein, a system for performing dynamic positron emission tomography (PET) includes a PET scanner device configured for configured for collecting volumetric radioactive measurement data associated with an administered radioactive tracer present in a target site of a subject over multiple scanning intervals and a magnetic resonance imaging scanner device configured for capturing a magnetic resonance (MR) image of the target site. The system further includes a dynamic PET platform comprising at least one processor, a memory element, and a dynamic PET engine stored in the memory element and when executed by the at least one processor is configured for receiving the MR image and the volumetric radioactive measurement data, performing a motion correction process to the volumetric radioactive measurement data to produce motion corrected PET data, co-registering the magnetic resonance image and motion corrected data to generate a co-registered dynamic PET volume; and applying a MCIF to the co-registered dynamic PET volume to calibrate an uptake amount of the radioactive tracer in the target site.

The subject matter described herein may be implemented in hardware, software, firmware, or any combination thereof. As such, the terms "function" "node" or "module" as used herein refer to hardware, which may also include software and/or firmware components, for implementing the feature being described. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The subject matter described herein will now be explained with reference to the accompanying drawings of which:

FIG. 9 is a flow chart illustrating an exemplary process for performing dynamic positron emission tomography according to an embodiment of the subject matter described herein.

DETAILED DESCRIPTION

Figure 1:
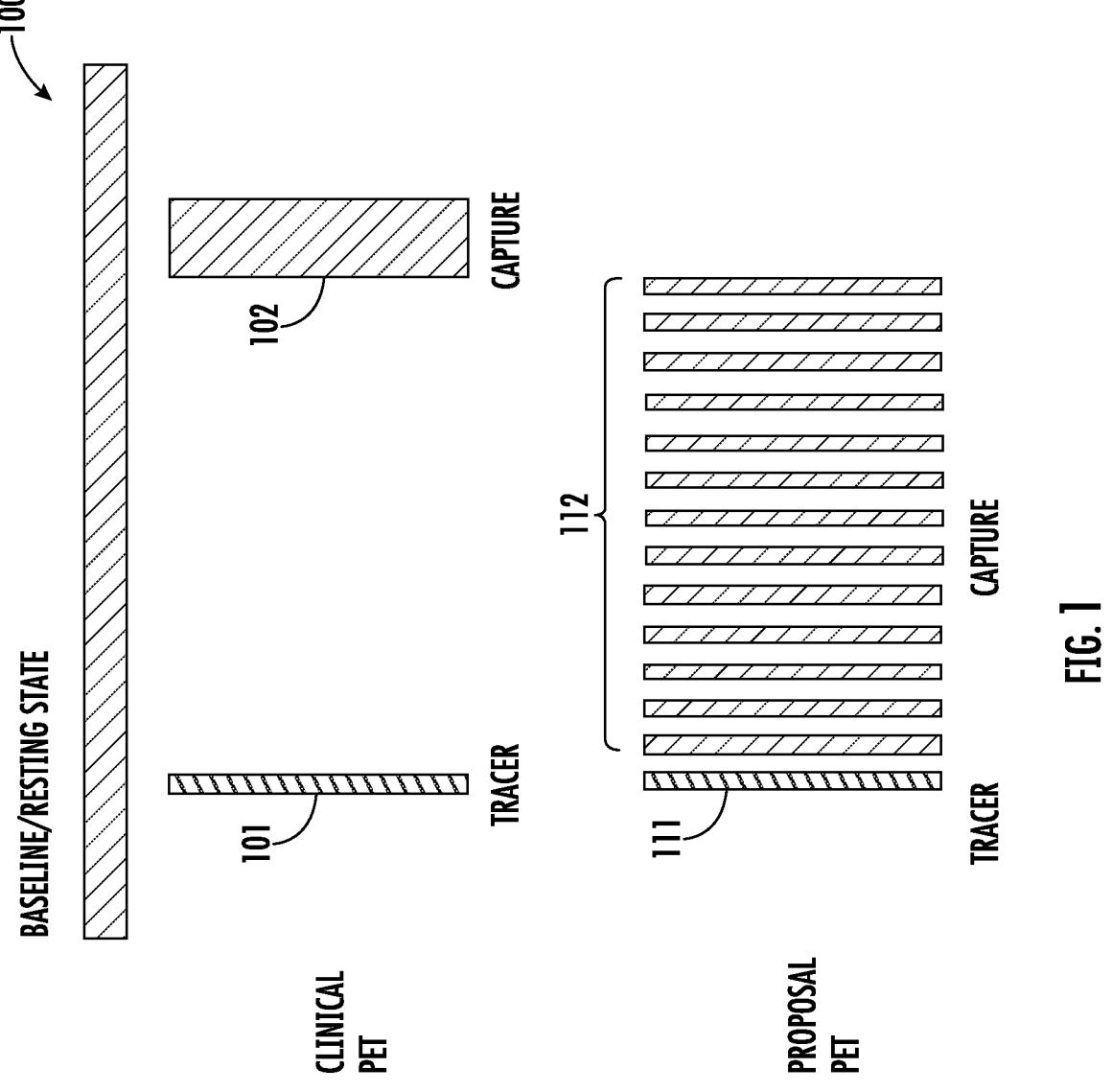
FIG. 1 is a block diagram contrasting the dynamic FDG-PET process from a clinical FDG-PET process.

The disclosed subject matter includes methods, systems, and computer readable media for performing dynamic positron emission tomography (PET). In particular, the disclosed subject matter pertains to a dynamic FDG-PET procedure that includes novel high-resolution parametric quantification methods that are utilized to better localize seizure foci. The goal of the disclosed subject matter is to demonstrate that changes in metabolic networks measured by dynamic PET will improve noninvasive identification of seizure focus and expand the number of patient candidates for transformative surgery.

As indicated above, static FDG-PET (e.g., static 2-[18F] fluoro-2-deoxy-D-glucose positron emission tomography, or sFDG-PET) has been utilized as one technique to conduct noninvasive stage of presurgical localization. In particular, PET with fluorine-18 fluorodeoxyglucose (18F-FDG) has been used for many decades to characterize patterns of brain glucose metabolism in normal language and cognition. Examples of abnormalities found in brain metabolism have been described in evaluation of brain tumors, traumatic brain injury, persistent vegetative state, dementias, and epilepsy. However, FDG-PET has exhibited limitations in spatial resolution and in sensitivity and specificity among the various pathologies that have been historically evaluated.

Namely, the disclosed subject matter relates to an alternative process of metabolic mapping, dynamic PET. This novel technology quantifies the dynamics of radiotracer uptake and decay in order to provide additional specificity or sensitivity in mapping of the desired metabolic activity in the target site (e.g., target organ). Although a number of different radiotracer types can be used, functional neuroimaging with 18F-FDG PET is described herein as an example. Further, the disclosed subject matter also presents the biomechanics of dynamic PET acquisition and processing as well as potential applications in neurological disease.

Dynamic Imaging Versus Static Imaging

As mentioned above, standard and/or static FDG-PET serves as a marker for glucose metabolism that is useful in providing pathophysiologic and diagnostic data in a clinical setting. The current standard of care for interpreting clinical FDG PET is qualitative visual analysis by performing comparisons between pathologic and normal appearing brain regions. Limitations of standardized update values (SUVs) include dependence on body weight and baseline blood glucose level.

In most instances, 18F-FDG acts as a competitive agonist to blood glucose and can be administered intravenously to a patient subject. Notably, 18F-FDG crosses the blood brain barrier, mimics glucose at the cross-membrane transport system, is taken into neurons, gets phosphorylated by hexokinase, does not metabolize further, and gets trapped as FDG-6-phosphate. At some point (e.g., typically 5 minutes up to 2 hours depending on the duration of useful tracer half-life), a volumetric map "snapshot" of radioactivity is acquired by the PET scanner. Biomathematical models interpret the volumetric map data to provide a quantitative, voxel-by-voxel, map with high counts indicating regions with the highest glucose use.

As illustrated in FIG. 1, the key variable returned by static clinical PET is the SUV. Notably, SUV is measured at a specific time point (see capture time 102 in FIG. 1) post the FDG injection (e.g., see radiotracer time 101 in FIG. 1) and can provide a semi-quantitative snapshot of glucose activity measure.

In contrast, the disclosed dynamic FDG-PET (e.g., dynamic 2-[18F] fluoro-2-deoxy-D-glucose positron emission tomography, or dFDG-PET) measures volumetric radioactivity on a continuous basis. In this paradigm afforded by the disclosed subject matter, the patient subject is scanned at pre-injection baseline 100, and the radioactive tracer (see tracer time 111) is injected during active scanning. Scanning continues for a continuous period (e.g., see capture period 112), much akin to a series of snapshots or movie frames that capture the changing concentrations of radiotracer per scanning interval. The process provides a data for kinetic models that measure, voxel-by-voxel, the rate and distribution of radioactivity uptake, decay, or radiotracer release. In the case of FDG-PET, kinetic processes may be a differentiating factor because abnormal tissues have a higher or lower concentrations of hexokinase resulting in a higher (hypermetabolic) or lower rate (hypometabolic) of glycolysis compared to normal tissues. The key variables which differentiates these kinetic processes are the rates of FDG uptake (e.g., in brain tissue), $K_i$ and metabolic rate of glucose uptake, MRGlu. Dynamic imaging captures the wash-in and wash-out of tracer kinetics from the point of injection as opposed to static imaging at a fixed point post tracer administration. Time-resolved dynamic FDG PET data enables computation of first pass tracer kinetics, $K_1$, kinetics of FDG from vascular to extra-vascular space, $k_2$, and finally trapping of FDG-6-phosphatase in the cellular spaces, $k_3$, which can be combined to compute rate of radioactive tracer uptake, or FDG uptake, $K_i=(K_1k_3/(K_2+k_3))$. In addition, $MRGlu=(K_i[Glu]/LC)$ can be computed (e.g., by the dynamic PET engine described below) and may take into account the competitive kinetics between FDG and blood glucose in the form of lumped constant, LC, where [Glu] is the average blood glucose level. These parameters may provide more insight into the glucose metabolic rates and metabolic vascular heterogeneity of epileptic foci.

Figure 2:
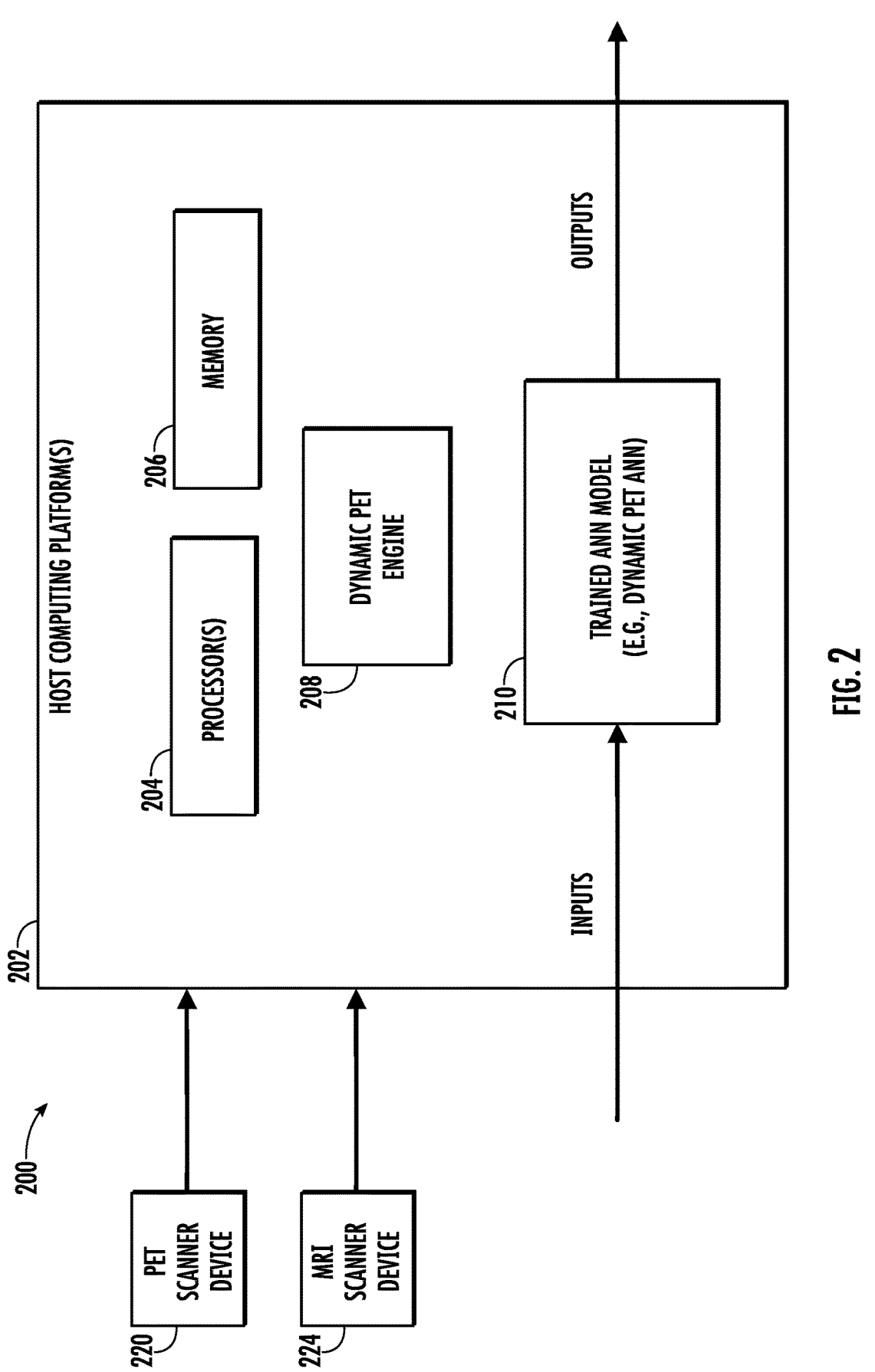
FIG. 2 is a block diagram of an example computing platform configured for performing dynamic positron emission tomography according to an embodiment of the subject matter described herein.

In some embodiment, the dynamic PET processing can be conducted using one or more host computing devices. For example, FIG. 2 is a block diagram of an example computer platform system 200 for performing dynamic PET and associated processes. It will be appreciated that FIG. 2 is for illustrative purposes and that various entities, their locations, and/or their functions may be changed, altered, added, or removed. For example, some entities and/or functions may be combined into a single entity. In another example, an entity and/or function may be located at or implemented by two or more entities.

In FIG. 2, system 200 may include one or more computing platform(s) 202 (e.g., a dynamic PET platform) having one or more processor(s) 204, such as a central processing unit (e.g., a single core or multiple processing cores), a microprocessor, a microcontroller, a network processor, an application-specific integrated circuit (ASIC), or the like. Computing platform 202 may also include memory 206. Memory 206 may comprise random access memory (RAM), flash memory, a magnetic disk storage drive, and the like. In some embodiments, memory 206 may be configured to store a dynamic PET engine 208 and a trained artificial neural network (ANN) model 210 (e.g., a dynamic PET ANN). Dynamic PET engine 208 may include one or more algorithms, software programs, software processes, and the like. As described below, dynamic PET engine 208 is configured to control, manage, and administer a plurality of processes corresponding to the execution of the disclosed dynamic PET methodology and functionality.

In some embodiments, dynamic PET engine 208 may be configured to receive image data from each of a PET scanner device 220 and/or a MRI scanner device 222. For example, PET scanner device 220 may include a Siemens Biograph time of flight (TOF) mCT scanner that can be utilized to perform dynamic acquisitions of a target site/organ, wherein the subject may be administered with an intravenous ~10 mCi radiotracer injection over 10 seconds with an initiation of a 60-minute scan in list-mode format. Further, MRI scanner device 222 may include a Siemens 3T scanner that is configured to captures a high resolution post-contrast T1-weighted MPRAGE MR images (256 pixels×256 pixels×192 slices).

Likewise, trained ANN model 210 may reside on memory of computing platform(s) 202 and be executable by processor(s) 204. Trained ANN model 210 may be configured to execute an automated segmentation method (e.g., segment out internal carotid arteries from dynamic PET data) and to identify epileptic seizure foci at the brain lobe level in the manner described below.

Figure 3:
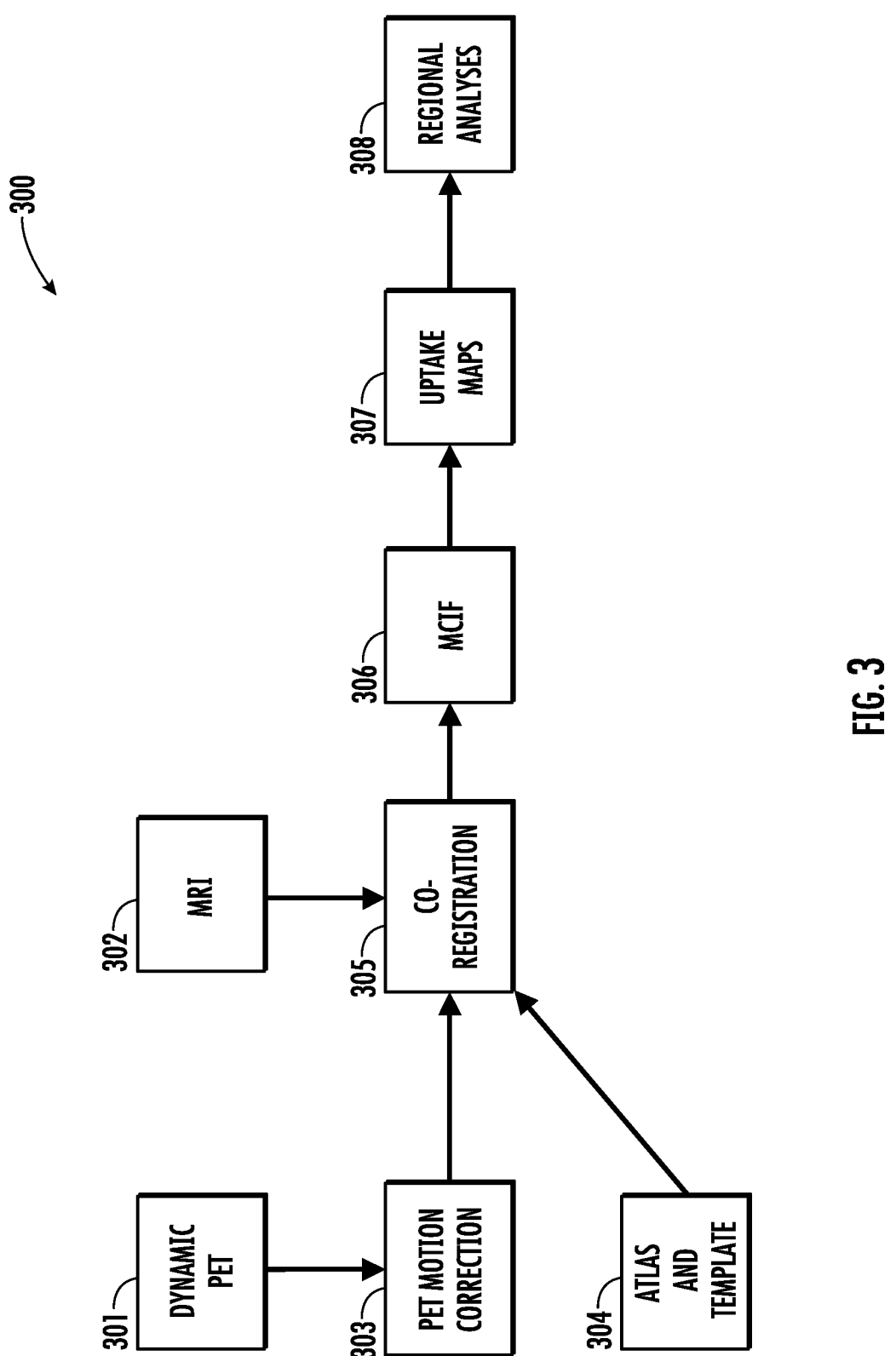
FIG. 3 is a block diagram illustrating an example imaging and analysis pipeline of a system configured for performing dynamic positron emission tomography according to an embodiment of the subject matter described herein.

As indicated above, dynamic PET engine 208 can be embodied as a software program, process, and/or algorithm that is configured to execute or manage the disclosed dynamic FDG-PET (dFDG-PET) and related processes. For example, FIG. 3 illustrates the example dFDG-PET processing, coordinating, and/or managing that can be conducted and/or managed by dynamic PET engine 208. Steps 301-304 of process 300 collectively illustrate example steps performed in dynamic FDG-PET image acquisition stage. In some embodiments, dynamic PET, high resolution MR and Destrieux Atlas defined on the MR brain template form the raw inputs. Moreover, steps 305-306 illustrate example pre-processing steps and steps 307-308 illustrate an example parametric map creation process.

For example, step 301 indicates that dynamic PET engine 208 is configured to receive image data (e.g., from a PET scanner device 220 in FIG. 2) that maps radiation over a consecutive series of time windows for a predefined amount of time (e.g., approximately 60 minutes). In some embodiments, subsequent analysis conducted dynamic PET engine 208 can be configured to deconvolute dynamic concentrations into a series of time-dependent "snapshots" (e.g., multiple scanning intervals) that reveal rates of glucose uptake rather than a final absolute uptake. More specifically, the dynamic uptake of radiotracer over an hour of acquisition time were deconvolved to pinpoint hypermetabolism defined as the lowest interhemispheric differences from mean uptake.

Figure 4:
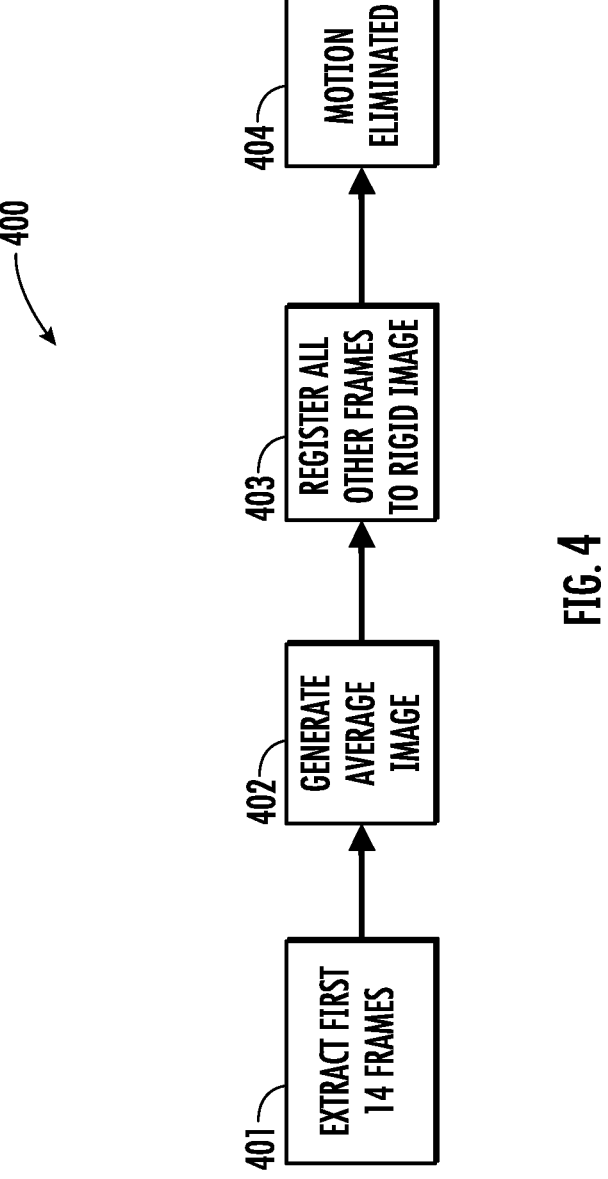
FIG. 4 is a diagram illustrating the steps for motion correction according to an embodiment of the subject matter described herein.

In some embodiments, dynamic PET engine 208 is further configured to conduct image pre-processing that entails performing motion correction for the 60-minute acquisition (see step 303). Notably, an exemplary motion correction process 400 is depicted in steps 401-404 of FIG. 4. In step 401, dynamic PET engine 208 is configured to extract a plurality of frames of the PET image data. For example, 14 frames can be extracted from PET data (e.g., 400 pixels×400 pixels×111 slices×38-time frames) collected by PET scanner device 220 in FIG. 2. Although the following description discloses the use of 14 frames, any number of frames that approximately accounts for the first 5-10 minutes of data can be used without departing from the scope of the disclosed subject matter. For example, the first 14 frames is typically used since that includes data that can be used to create an average image and wherein minimal head motion is expected. Notably, some other number/range of frames may be acceptable if there is no head motion. In some instances, the time series data can be evaluated to visually assess if there is any head motion anytime during the hour long scan. Frames corresponding to first 10 minutes (e.g., typical static scan) may be acceptable, to create an average image, wherein there is expected to be minimal or no head motion.

In step 402, an average image is generated. For example, the dynamic PET engine 208 can be configured to average the PET data across the extracted 14 frames to create a reference that is used to perform a rigid body transform across the 38 frames of the PET data. The average of all the motion corrected PET frames were also resliced and subsequently co-registered (e.g., see step 403) with the MRI image (e.g., see MRI data acquired in step 302 in FIG. 3) of the target site/organ (e.g., MRI data generated by MRI scanner device 224). In some embodiments, the resliced PET frames may be co-registered with a T1-weighted MRI using non-rigid transform to generate a transformation matrix (which may be utilized to co-register the subject's PET data with a subject's MR image). This transformation matrix is used, in turn, by dynamic PET engine 208 to generate a co-registered dynamic PET volume (and/or dynamic PET data). At this stage, motion is eliminated from the PET data (see block 404).

Returning to FIG. 3, dynamic PET engine 208 is further configured to generate an atlas and template. For example, MRI image data can be co-registered with a high-resolution T1-weighted MRI template (e.g., a template provided by the Montreal Neurological Institute (MNI) using a non-rigid transform, and a second transformation matrix can be generated (which can be used to bring the masks of a Destrieux atlas defined on the MR brain template from the MNI to the subject's MR space). For example, all of the 164 regions of a Destrieux atlas, which is defined on the same MR brain template, may be binned to generate 36 regions of interest (e.g., 18 regions/side). The second transformation matrix can be inverted (e.g., by dynamic PET engine 208) and applied to all ROIs to transfer them from the standard MNI template into the patient MRI (e.g., step 305 in FIG. 3). The ROIs can then be applied by dynamic PET engine 208 onto the parametric maps (e.g., voxel-by-voxel maps) generated from dFDG-PET images during the co-registration stage shown in step 305 in FIG. 3.

Figure 5:
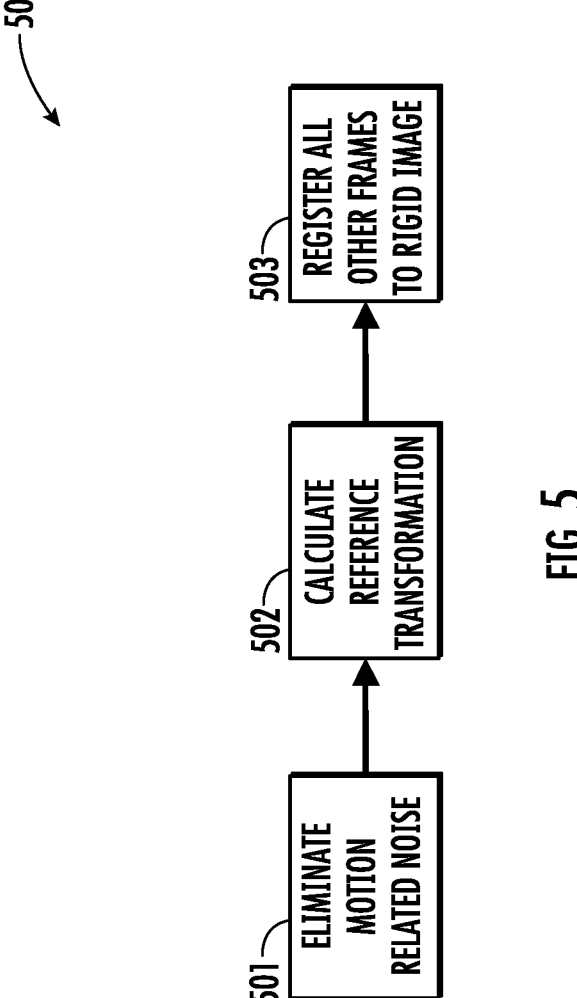
FIG. 5 is a diagram illustrating the steps for performing dynamic PET MR co-registration according to an embodiment of the subject matter described herein.

FIG. 5 illustrates a diagram depicting an example process 500 for performing a dynamic PET MR co-registration operation. In step 501, the dynamic PET engine is configured to motion correct the collected dynamic PET data to eliminate motion related noise present in the data. In step 502, a reference transformation is calculated by co-registering the average (averaging across all time frames) motion corrected PET volume with a T1-weighted MRI using non-rigid transform to generate a transformation matrix. In step 503, the dynamic PET engine is configured to apply the reference transformation (e.g., a transformation matrix) across all time frames to generate a co-registered dynamic PET volume in the MR subject space (i.e., the MR of the target site/organ). For example, the dynamic PET volume is applied in the MR space (e.g., via the first transformation matrix) and the masks are also defined in the subject's MR space (e.g., via a second transformation matrix). As such, both PET volume data and masks are applied in the subject's MR space.

Figure 6:
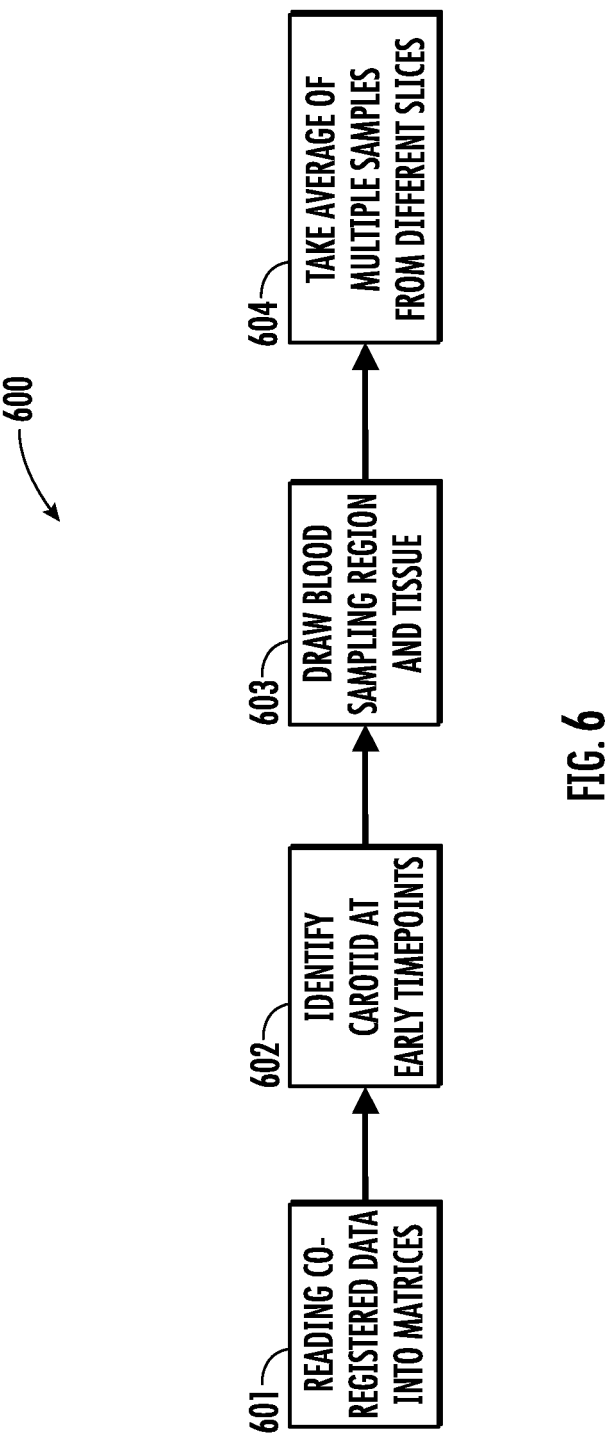
FIG. 6 is a diagram illustrating the steps for generating an image-derived blood input function according to an embodiment of the subject matter described herein.
Figure 7:
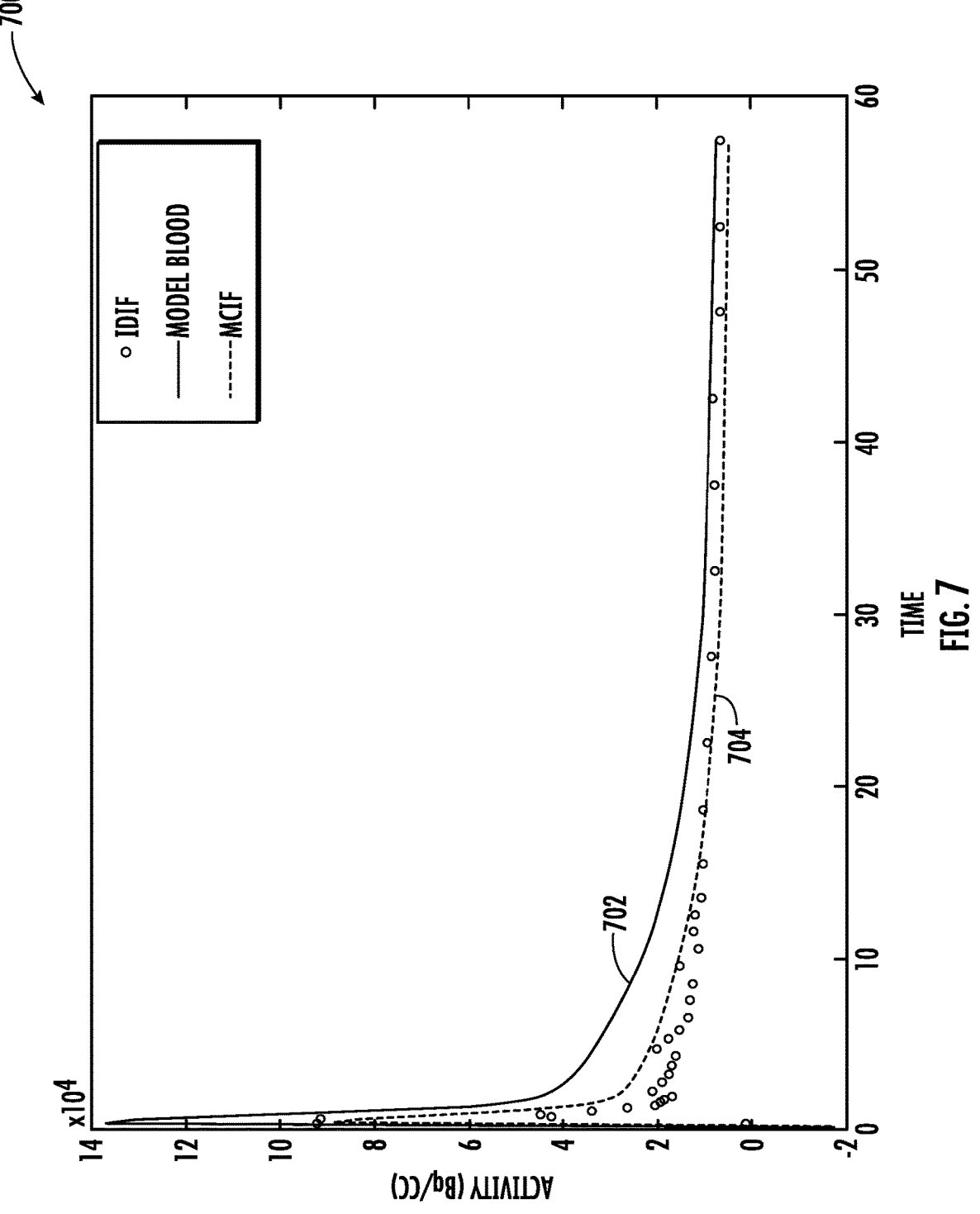
FIG. 7 is a graph of a model corrected blood input function according to an embodiment of the subject matter described herein.

Returning to FIG. 3, step 306 indicates that a dynamic PET engine is also configured to generate objective parametric PET maps from a model corrected blood input function (MCIF). Notably, the dynamic PET engine is configured to initially generate an image-derived blood input function (IDIF) from which an MCIF can be computed. FIG. 6 illustrates a diagram depicting an example process 600 for generating an IDIF. In step 601, the dynamic PET engine is configured to read the co-registered PET data into matrices. In step 602, the internal carotid arteries are identified at the early time frames (within 16-20 seconds of tracer administration) to capture the wash-in and wash-out kinetics of the tracer from the blood. In step 603, the dynamic PET engine is configured to draw a blood sampling region and tissue. In step 604, the dynamic PET engine is configured to compute an average of multiple samples from different PET frame slices to generate a plurality of blood time activity curves of a model IDIF. Optimization of the IDIF's model equations/curves can be used by the dynamic PET engine to yield an estimation of the MCIF (as shown in FIG. 7 and described in greater detail below).

In some embodiments, the MCIF is corrected for partial volume (PV) averaging and spill-over (SP) contamination. For example, an image-derived blood input function (IDIF) from an internal carotid artery in an early time frame for each subject can be computed by dynamic PET engine 208 from the cohort average of 4 regions of interest (ROIs) of the left internal carotid artery. These ROIs can be applied (e.g., by the dynamic PET engine) to all the motion-corrected 38 PET frames to generate blood time activity curves (PET$_{IDIF}$). Although 4 ROIs and 38 PET frames are described herein, the use of any number of frames and any number of ROIs can be utilized without departing from the scope of the disclosed subject matter. In some embodiments, a model IDIF correcting the blood input for PV and tissue SP contamination can be represented as:

$$\text{Model}_{IDIF,i} = \frac{\int_{t_b^i}^{t_e^i} [S_{TB} C_T(t) + r_b C_a(t)] dt}{t_e^i - t_b^i},$$

in which $S_{Tb}$=SP contamination from the tissue to the blood at late time points, $r_b$=blood recovery coefficient, $t_b$ and $t_e$=beginning and end of a time frame. Further, $C_T(t)$, the model tissue, was obtained by solving FDG transport differential equations from blood to tissue spaces as described. In addition, $C_a(t)$ is 7-parameter model blood for FDG transport as described. The above model IDIF was optimized using the following objective functions:

$$O_1(p) = \sum_{i=1}^{n} (\text{Model}_{IDIF,i} - PET_{IDIF,i})^2$$

$$O_2(p) = (\text{ModelPeak}_{IDIF} - PETPeak_{IDIF})^2$$

$$O(p) = O_1(p) + O_2(p)$$

In some embodiments, ModelPeak was computed (e.g., dynamic PET engine) from the model equations for the IDIF (see equation for Model$_{IDIF}$ above). PETPeak values were derived from the dynamic PET blood images for each patient subject. Optimization of $O(p)$ may use non-linear regression analysis yielding the estimate of MCIF (see plot 700 in FIG. 7). For example, FIG. 7 illustrates an example computed model corrected blood input function (MCIF) correcting for partial volume effects (PV) and spill over (SP) contamination. IDIF is obtained from the dynamic PET images (curve with circles) and model IDIF (curve 702) accounts for PV and SP contamination to generate MCIF (curve 704).

Each voxel of the dynamic PET data may subsequently be independently fed by the dynamic PET engine into a 4 parameter 3-compartment kinetic model, together with the computed MCIF to compute whole brain parametric ($K_1$, $k_2$, $k_3$, $K_i$ and TBV) maps using the following equation:

While the blood IF can be captured through arterial sampling in animal models, a non-invasive approach is preferred for humans so as to avoid the associated risks (e.g., arterial occlusion and infection) with arterial sampling. Not only is arterial sampling potentially dangerous for both experimental animals or human subjects, but this could compromise the pathophysiology of the animal or subject being imaged, resulting in unreliable computation of kinetic rate constants and hence net influx constants or total distribution volumes.

$$C_m(t) = \frac{1}{(t_2 - t_1)}$$

$$\int_{t_1}^{t_2} \left\{ (1 - TBV) \left[ \frac{K_1 k_3}{k_2 + k_3} \int_0^T C_a(u) du + \frac{K_1 k_2}{k_2 + k_3} \int_0^T C_a(u) \cdot e^{-(k_2 + k_3)(T-u)} du \right] + TBV \cdot C_a(T) \right\} dT$$

where Ca(t) is the computed MCIF and $K_1$-$k_3$ are the kinetic parameters and TBV is the total blood volume accounting for the spill-over contamination from the blood to the tissue at the early time points and (1-TBV) accounts for the partial volume averaging for the tissue voxel. $C_m(t)$ is the measured tissue voxel time activity curve. In some embodiments, parallelization of multicore high-performance computers can be used to compute whole-brain parametric maps for all patients.

In step 307, update maps are computed by the dynamic PET engine. For example, each voxel of dynamic PET data along with blood input is independently fed into a graphical Patlak model to compute parametric $K_i$ maps using linear regression and subsequently z score maps. Specifically, whole brain voxel-level rate of FDG uptake ($K_i$) can be computed from the motion-corrected, co-registered dFDG PET data for each patient subject. $K_i$ maps for each patient can be converted (e.g., by the dynamic PET engine) to voxel level z-score maps by normalizing to the whole brain mean and standard deviation within each patient subject. Average regional z-scores were computed for 36 regions of interest (e.g., 18 regions/side). All regions with z-scores less than −1.65 standard deviations (SD), dictated by the default z-score threshold in MIM (https://www.mimsoftware.com/), were identified as hypometabolic compared to its contralateral side.

In the case of FDG-PET, the process of calculation allows construction of a 4D model of hexokinase activity, glucose use, and signal decay within the period of scanning. The key, therefore, in pilot studies of clinical validation are to explore where critical time points of inflection in glucose kinetics that differentiate normal from abnormal neuronal activity. Evaluation of these dynamic properties, however, requires development of rigorous reference values.

In step 308, the dynamic PET engine is configured to conduct regional analyses. For example, the dynamic PET engine may use the co-registered template and atlas to bin individual voxels of the generated uptake maps for regional analyses.

Model Corrected Blood Input Function

In some embodiments, the calculation of tracer kinetics can be performed by the dynamic PET engine and requires the capturing of a reference value of blood tracer concentration, the blood input function (IF). The blood IF describes the level of radiotracer within the subject's blood that is available for tissues to use, as a means of calibrating regional dynamic glucose changes. More specifically, tracer uptake can be calibrated with a model corrected blood input function with partial volume corrections to generate tracer parametric maps compared between mean radiation values between hemispheres with z-scores. The regions of interest (ROI) with the lowest negative z scores (<−1.65 SD) are identified as hypometabolic.

In some embodiments, the blood input function can be continuous intraarterial blood sampling over the whole period of PET acquisition. Practically, however, continuous intraarterial monitoring requires catheterization of a major artery such as the carotid or femoral artery of the subject.

As such, the blood input function can be calculated (e.g., by dynamic PET engine) from the subject through the acquired image(s). For example, the image-derived blood input function (IDIF) has been developed, wherein the imaged inferior vena cava or the left ventricular blood pool can be used as sources of IDIF for computing cerebral FDG uptake rates in animals. These areas serve as large, unambiguous sites that contain a readily accessible pool of blood that contains the maximal concentration of radiotracer for calibration of the "ceiling" of radiation. The radioactivity recorded here serves as the representative "maxima" for uptake in the brain.

Human brain imaging, however, does not offer easy regions for calculation of the IDIF. State-of-the-art PET scanners allow a limited field of view (e.g., 23 centimeter axial field of view) meaning that a brain image cannot contain body blood "pools" as in small animal subjects. Consequently, only the internal or external carotid arteries are large enough for computation of the IDIF. However, the carotid arteries are small (~6-7 mm) compared to the PET scanner's spatial resolution (~4-5 millimeters full width half maximum (FWHM)). Therefore, accurate calculation of the IDIF can be impaired by partial volume averaging (PV) or cross-contamination or spillover effects (SP) by the inability to separate carotid contents from surrounding extracarotid tissues.

In some embodiments, practical dynamic PET imaging is configured to accurately record the IDIF in an unsedated human subject. For example, a dual output model that corrects for PV and SP contamination and peak fitting optimization functions for computation of the MCIF can be utilized by the disclosed subject matter. In some embodiments, the dynamic PET engine executes a 15-parameter dual output model, which is a minimization (optimization) of a parametric formulation of time-dependent blood and the surrounding tissue radioactivity concentrations obtained from dynamic PET images.

For example, the disclosed dynamic PET engine can be configured to execute cerebral K modeling. Brain TACs for four super regions (e.g., Cerebellum, Striatum, Cortex, and Hippocampus) can generated through the application of a T2 rat brain atlas onto dynamic PET images using PMOD (pixel-wise modeling, pmod.com). Volumes and average TACs may be computed for a total of 58 volumes of interest (VOI) consisting of 26 regions split into two different hemispheres (Left (L)/Right (R)), and an additional 6 regions without lateral split. Thirty-five (35) of these VOIs may be binned and combined to generate volumes and average TACs for the four super regions. The fifty-eight (58) regions generated directly from the atlas, as well as the four super regions, can be analyzed in Matlab (Mathworks Inc., Natick MA) and/or the dynamic PET engine. Kinetic modeling for all regions may be completed using a 4-parameter compartment model described below.

Modified Objective Function

In some embodiments, a 15-parameter dual output model with SP and PV corrections optimized the following objective functions:

$$O_1(p) = \sum_{i=1}^{n} [(\text{Model}_{IDIF,i} - PET_{IDIF,i})^2 + (\text{Model}_{myo,i} - PET_{myo,i})^2]$$

$$O_2(p) =$$

$$[(ModelPeak_{IDIF} - PETPeak_{IDIF})^2 + (ModelPeak_{myo} - PETPeak_{myo})^2]$$

$$O(p) = O_1(p) + O_2(p)$$

where Model DIF, $\text{Model}_{myo}$ are model output equations (see equations below) and $PET_{IDIF}$, $PET_{myo}$ are image derived blood and myocardium time activity curves.

$$\text{Model}_{IDIF,i} = \frac{\int_{t_b^i}^{t_e^i} [S_{mb} C_T(t) + r_b C_a(t)] dt}{t_e^i - t_b^i}$$

$$\text{Model}_{myo,i} = \frac{\int_{t_b^i}^{t_e^i} [r_m C_T(t) + S_{bm} C_a(t)] dt}{t_e^i - t_b^i}$$

$S_{mb}$ and $S_{bm}$ are SP contamination factors from the myocardium to the blood and vice versa; $r_b$ and $r_m$ are recovery coefficients for blood pool and myocardium, respectively, and $t_b$ and $t_e$ are the beginning and end of a time frame. $C_T(t)$, the model tissue, is obtained by solving FDG transport differential equations from blood to tissue spaces. $C_a(t)$ is 7-parameter model blood for FDG transport as described.

The second objective function, $O_2(p)$ minimizes the square of the difference between the model and image-derived blood and myocardium peak values. The ModelPeak was computed from the model equations for the IDIF (Model_IDIF) and myocardium (Model_myo). The PET-Peak values were derived from the dynamic PET images for both the blood and the myocardium for each rat test subject. Optimization of the objective function, $O(p)$, using non-linear regression analysis written in Matlab, resulted in estimation of MCIF, which was then used to compute cerebral Ki, defined as $$K_i = \frac{K_1 k_3}{(k_2 + k_3)},$$

using a 4-parameter compartment model, $$C_m(t) = \frac{1}{(t_2 - t_1)}$$

$$\int_{t_1}^{t_2} \left\{ (1 - TBV) \left[ \frac{K_1 k_3}{k_2 + k_3} \int_0^T C_p(u) du + \frac{K_1 k_2}{k_2 + k_3} \int_0^T C_p(u) \cdot e^{-(k_2 + k_3)(T-u)} du \right] + \right.$$

$$\left. TBV \cdot C_p(T) \right\} dT.$$

Notably, the computed area under the curve (e.g., AUC under MCIF) and $K_i$ were compared to that derived from arterial blood samples. The disclosed subject matter refers to AUC as direct and downstream K as indirect comparisons.

In some embodiments, this results in simultaneous optimization of the 7-parameter blood input function (see, e.g., MCIF plot 704 in FIG. 7) accounting for corrections for cross-contamination (SP) and radioactivity recovery (PV) and the tissue kinetic parameters to compute downstream rates of tissue FDG uptake ($K_i$). In some embodiments, the computation of MCIF (e.g., by dynamic PET engine) is a semi-automated process with apriori determination of the lower and upper bounds and the initial guess values of the 15 parameters, which has been validated with arterial blood sampling in rodent total body dynamic PET imaging. Further, the above deterministic interior reflective Newton algorithm when combined with stochastic artificial immune network resulted in robust estimation of MCIF and downstream $K_i$ independent of the bounds.

In some embodiments, the dynamic PET engine may also be configured to further improve the dual output model and compute MCIF by parsing through the internal carotid arteries from the image within a subject and across a plurality of other subjects to compute a Population based Blood Input Function (PBIF) from existing dynamic FDG brain PET data. The PBIF obtained by further optimizing MCIF with additional cost functions based on peak fitting and venous blood samples may be used as a standard blood input for computing high resolution parametric whole brain maps in normal and abnormal functional brain networks non-invasively.

Model based methods described herein for estimating PBIF are time consuming, operator dependent, and require training to find samples for blood input function as well as to verify a time activity curve (TAC). As such, the disclosed subject matter entails a completely automated method for retrieving carotid blood input directly (e.g., via an Automatic image derived blood Input Function (AIF) executed by the dynamic PET engine) from a high-resolution dynamic PET image. In some embodiments, this may be accomplished by a dynamic PET engine using a deep feed forward neural network. Such a neural network may receive the entire dynamic image as an input and identify voxels which can be used as members of the blood input regions of interest (ROI). In recent years, artificial neural networks (ANN) have become popular and been optimized for classification of problems due to their ability to define relationships between features that are difficult for humans to visualize. The ANN has been utilized in combination with Bayesian information criterion or multi-resolution analysis for determination of PET volume. However, none of these approaches qualitatively utilized the dynamic temporal tracer uptake values. Notably, the disclosed subject matter pertains to the training of the model on time activity curves from each voxel from dynamic PET images across a group of subjects, which can yield millions of samples of labeled data for a robustly trained algorithm. Notably, the dynamic PET engine can be configured to provide a fully automated method for correctly identifying the carotid arteries in dynamic PET images, allowing researchers to save time spent on drawing, redrawing, and validating time activity curves. In addition, the model will identify all voxels relevant to the region of interest, making the blood input more robust to noisy areas and more representative of the whole region. Lastly, the robustness of neural networks to random error will allow the neural network to be trained on data drawn manually with slight variations between researchers, but can provide results with high reproducibility.

Although artificial neural networks (ANN) are increasingly becoming popular in modeling dynamic PET reconstruction, their application as an automated segmentation tool with time resolved PET images has been limited. Dynamic PET is a relatively new imaging modality, given the scarcity of data publicly available for training large scale machine learning models. In some embodiments, the dynamic PET engine can be configured to execute an ANN combined with the time activity curves of each voxel to segment abnormalities (e.g., tumors) in vivo from dynamic FDG PET images.

This disclosed subject matter is innovative for at least the following reasons:

1) Development of a PBIF by optimizing MCIF. A model corrected blood input function (MCIF) in a dual output model may be optimized for the first time in human dynamic brain PET imaging.

2) Development of optimized MCIF. Further optimization of MCIF using additional cost functions of peak fitting and venous blood samples in human dynamic brain PET imaging is novel.

3) Development of new 140 million sample data set labeled for carotid identification and model training. This dataset may be developed through the manual segmentation of high-resolution dynamic PET data from a plurality of subjects, with each timepoint activity level used as a feature for training.

4) Development of new feed forward networks specific to classification of dynamic voxels. This application of a deep feed forward network may be optimized through testing a matrix of activation functions, learning rates, layer dimensions, and error reduction techniques. This network can also help to overcome the challenge of learning an imbalanced dataset using resampling techniques.

5) Final output of voxel level localization of the carotid arteries. This approach using PET data alone may provide higher precision and faster calculation than MR co-registration techniques. This neural network can also enable automatic segmentation of the carotid arteries (e.g., via an Automatic image derived blood Input Function (AIF)) from inherently low signal PET images, without any co-registration or reslicing which can introduce error.

6) Development of compartment models. Compartment models with spillover and partial volume corrections from dynamic brain PET images captured with the aforementioned PBIF and AIF to compute high resolution whole brain parametric maps (as opposed to graphical models) in human temporal lobe epilepsy is novel.

7) Development of a feed forward neural network using a combination of metrics from both dynamic PET and MR image datasets for identifying epileptic seizure foci at the lobe level is novel.

Research Design

As indicated above, the dynamic PET engine can be configured to conduct an MCIF computation from dynamic human FDG brain PET. To compute MCIF from the internal carotid arteries from dynamic FDG brain PET data, regions of interest will be drawn (e.g., indicated) on the internal carotid arteries and around the brain (e.g., 30/side of the brain) within a subject to generate average image derived blood input function and tissue time activity curves. A 15-parameter dual output model with SP and PV corrections may be optimized to generate MCIF. In some embodiments, a cost function with a venous blood sample obtained at the last time point is introduced, to further optimize MCIF. The disclosed subject matter has last time point venous blood samples for all (e.g., 33) dynamic FDG PET datasets. The cost function may be introduced as:

$$O_3(p)=(C_a(t_s)-b)^2$$

$$O(p)=O_1(p)+O_2(p)+O_3(p)$$

Notably, $C_a(t_s)$ is a parametric formulation of the blood input function as described and b is a venous blood sample at the last time point. Optimization of the new objective function may result in robust computation of the MCIF within a subject and hence PBIF across subjects.

In some embodiments, the ANN algorithm utilized by the dynamic PET engine can be trained with constructed training data sets. For example, a training dataset can be built from dynamic PET images from 33 subjects across two disease models obtained using the Siemens TOF Biograph mCT scanner. These images will be corrected for motion using MRTrix3 functions as described above to rigidly transform each timeframe volume to an average volume of the first 14 time-frames, which are assumed to be without motion. Motion corrected subject volumes will then be loaded into MATLAB (Mathworks Inc., Natick MA) for manual segmentation. In MATLAB, an early timeframe volume will be manually parsed for each image, when the tracer is most concentrated in the blood. Regions of interest (ROI) will be drawn (e.g., indicated) around the left and right internal carotid arteries across the roughly 60 slices where they are apparent. Voxels across all slices of all images which fall into the carotid ROIs will be labelled and their time activity curves will be reshaped into a two-dimensional matrix, with each voxel activity curve making up one sample row, and each timepoint providing a feature column. All remaining voxels which are nonzero when summed across all timepoints will be added to the matrix and labelled as non-carotid. Voxels whose time-wise sum is zero will be ignored, which will throw out the large component of the PET volume containing no subject matter. Because neural networks are known to be robust to random labelling error, it is expected that random variation in region drawing resulting from different researchers drawing regions will have little effect on the final accuracy of the model. The final dataset will be a two-dimensional matrix consisting of roughly 140 million samples (voxels) across 38 features (timepoints). Although these data will be heavily imbalanced, with a ratio of carotid voxels to other voxels expected to be 1 to 10,000, the ANN can seek to overcome this imbalance using a variety of resampling techniques. This dataset will be uploaded into a python script where the final model will be assembled using neural network construction packages tensor-flow and scikitlearn.

Training Split and Imbalance Correction

In order to correct for the significant imbalance in the two classes, the synthetic minority oversampling technique (SMOTE) can be applied to up-sample the carotid TACs without generating exact copies of samples, which might lead to overfitting. The full up-sampled dataset will be split into three major subcategories using two separate steps. First, 75% of the data will be randomly selected for training, while the remaining 25% will be reserved for final testing. The training set will then be split again with the same distribution into true training and validation sets.

Model Development

Figure 8:
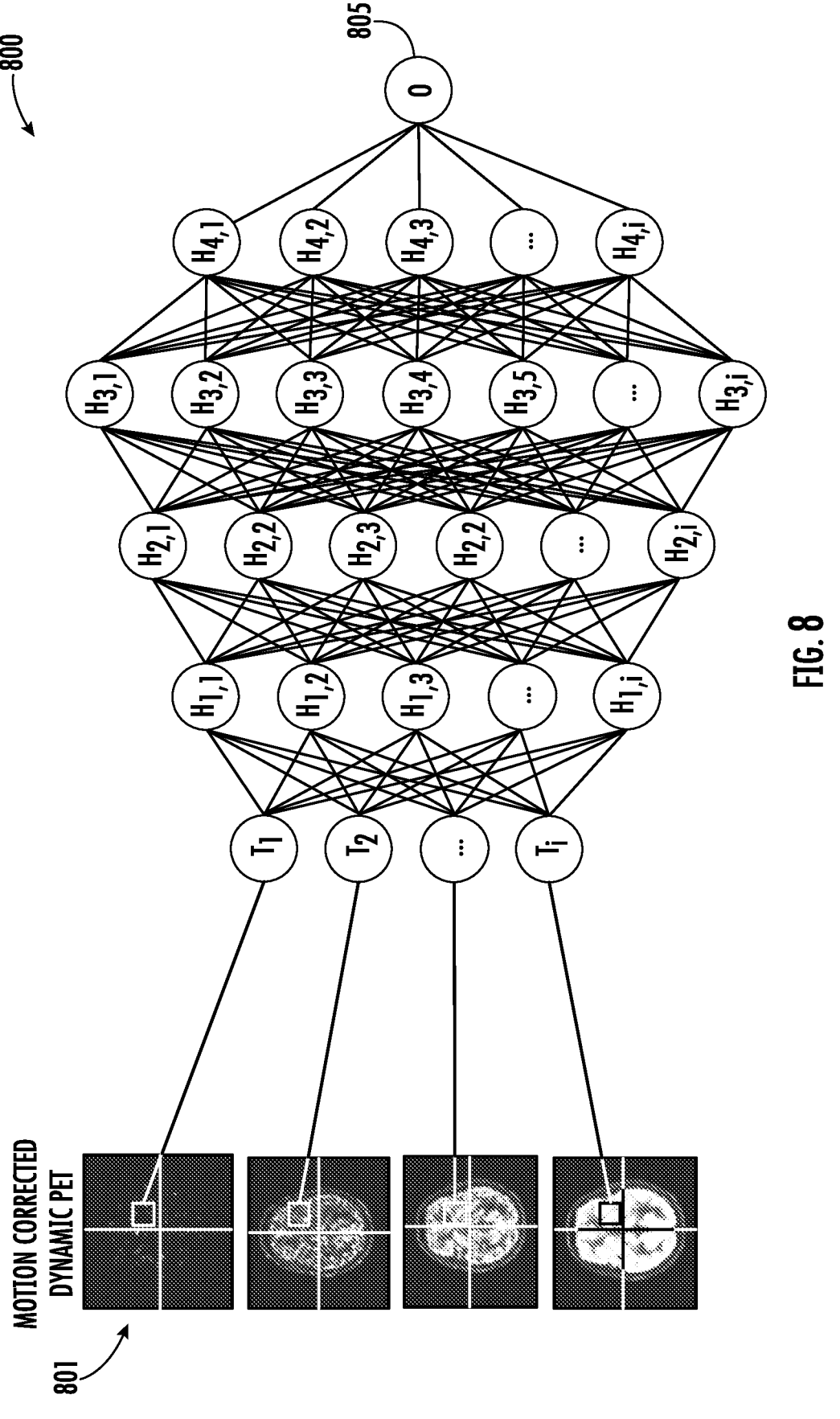
FIG. 8 is a diagram of a model framework of a deep forward feed artificial neural network configured for performing dynamic positron emission tomography according to an embodiment of the subject matter described herein.

A neural network model for binary classification can be developed for the voxel-wise dataset by gradually adjusting components of a deep feed-forward network as shown in FIG. 8. In particular, FIG. 8 illustrates a model neural network framework 800 that comprises a deep forward feed neural network (e.g., trained ANN model 210 in FIG. 2). For example, each voxel of the dynamic PET data (e.g., motion corrected dynamic PET data 801) may be submitted as a single input, with the voxel activity at each timepoint making up the features ($T_1$-$T_i$). The network will be initialized with four hidden layers ($H_1$-$H_4$) whose nodes will employ leaky ReLU activation functions, and finally output through a single sigmoid activated node. A series of iterations may be used to test for the optimal set of parameters within this framework to generate the most optimal validation metric, which will be selected based on the final distribution of samples after minority class up-sampling is complete. The final output 805 will be a binary classification of either carotid or not carotid. Once the model is complete, an image can be inputted and the carotid voxels automatically identified for generation of an accurate total volume blood input.

In some embodiments, the voxel-wise dataset can be split twice for training and validation. Iterative testing of model parameters including depth, number of nodes per layer, activation function, learning rate, connectivity, weight initialization, dropout, and training epochs will yield an optimized model according to validation metrics. The model will be initialized to 4 hidden layers, each with between 100 and 200 nodes. All nodes will use the leaky rectified linear activation unit (Leaky ReLU), and will be optimized using stochastic gradient descent with a learning rate of 0.1 with no dropout and full connectivity over 30 epochs. Because SMOTE will be applied to better balance the category sizes, accuracy will be used as an initial validation metric for model training, however a series of validation metrics will be generated and monitored during training to track mode progress and avoid underfitting and overfitting. Once an optimal validation metric is achieved, the final model will be tested using the remaining 25% of the initial dataset to provide an overall performance metric.

The use of reference tissue models obviates the need for image-derived blood sampling from the carotid arteries, wherein the cerebellar grey matter serves as a reference region and has been found to reliably assess tracer uptake rates or binding potential in several cerebral abnormalities. However, the pathophysiology of a number of these conditions violates the assumption underlying reference tissue models in that no single brain region can be used as a reference region, as no region can be assumed to be devoid of FDG uptake.

Graphical models have been used as simpler approximations of the rigorous 2T non-reversible and reversible kinetic models, respectively. The graphical models involve simple linear optimizations as opposed to the non-linear optimizations of the kinetic parameters for the latter. This enables faster computation of whole brain parametric maps, which otherwise would take hours using the rigorous models. However, the latter provides more information related to the individual kinetic parameters including first pass rate coefficients, rates of trapping, binding potential, and distribution volume ratios, which otherwise cannot be estimated using the simple graphical models.

In some embodiments, the disclosed subject matter aims to provide novels methods for quantitative evaluation of image derived blood input function from dynamic brain PET images. Novel algorithms for non-invasive computation of cellular metabolic function from high resolution dynamic FDG PET images of the brain are presented. For example, as indicated above, a PBIF with spill over and partial volume corrections may be utilized by the disclosed subject matter. Calibration of brain cellular metabolic activity requires semi-automatic methods to delineate the internal carotid arteries for non-invasive computation of blood input function. The steps can include motion correction of dynamic PET data sets, followed by co-registration with MR data sets to generate motion correct-ed co-registered dynamic PET volumes. Regions of interests (ROI) may be drawn on the internal carotid arteries and around it to generate average image derived blood input function and tissue time activity curves. A 15-parameter dual output model will then be optimized to generate a MCIF. Additional cost functions based on peak fitting and venous blood samples will be introduced to optimize MCIF. In some embodiments, an average of MCIFs can be used to generate a PBIF.

In some embodiments, the dynamic PET engine and/or dynamic PET ANN is configured to execute an automated segmentation method. For example, the executed automated segmentation method may be based on a Deep Feed-Forward (DFF) artificial neural network (ANN) that is configured to segment out the internal carotid arteries from dynamic PET data. The ANN may be created and trained using training sets and testing sets of previous subjects. Notably, training data set data can be developed by drawing ROIs on the carotid arteries for the subjects (~60 regions/subject (left and right side)×voxels per region at each time frame). The time activity curve (TAC) for each voxel can serve as an input, with the FDG activity at each time-point used as the feature set. The binary masks generated from drawing ROIs can be used as the labels. In some embodiments, the dynamic PET engine can be configured to perform testing on TACs derived at a voxel level for a plurality (e.g., 10) of test subjects for automatic identification of the carotid arteries to determine an automatic image derived blood Input Function (AIF).

The disclosed subject matter further features the notion of compartment modeling. For example, improved algorithms based on compartment models with spill over and partial volume corrections are presented. The disclosed subject matter may evaluate findings in comparison with graphical Patlak models for high resolution parametric computation of whole brain maps in a pilot study of dynamic FDG brain PET imaging of 10 subjects with intractable focal epilepsy. Further, PBIF and AIF can be optimized and utilized for the compartment model computations.

In addition, the ANN (or another separate feed forward ANN on computing platform 202) may also be configured to identify epileptic seizure foci at the brain lobe level. In some embodiments, dynamic PET engine can use a combination of metrics from both dynamic PET and MR images. These metrics may include the compartment model parameters, rate of FDG uptake, and regional volume as a robust feature set. In some embodiments, the ANN model can be trained and evaluated using comparison with EEG video findings.

The static applications of brain PET imaging used in the clinical routine have limitations. For example, in a longitudinal study investigating the value of presurgical tests, PET-based identification of seizure foci predicted one year seizure-remission with clinically useful odds ratios, but odds ratios were lower than other localizing methods such as ictal SPECT, the presence of pre-operative auras, or concordance among pre-surgical procedures. In another example, when focal hypometabolism demonstrated on PET is ipsilateral to the side of the presumed seizure focus, seizure-free outcomes in those with otherwise unknown foci are similar to those in patients with lesional temporal lobe epilepsy. The role of PET becomes especially important because 20-40% of patients in recent surgical series lacked clear MRI lesions. The identification of a metabolic abnormality that were closely correlated with other evaluations of the surgical focus was associated with better postoperative seizure control. When focal PET hypometabolism was present without an MRI abnormality, the surgical outcome was equivalent to those with clear MRI lesions. In those with normal MRI and discordant noninvasive data, PET aids in triaging; for example, 63% of patients with normal MRI and discordant data had focal PET abnormalities; of those, 41% went on to have invasive monitoring or epilepsy surgery guided by PET. One goal of the disclosed subject matter is to demonstrate the improved diagnostic yield of newly developed dynamic PET quantification methods based on compartment models and deep feed-forward neural networks to accurately localize the seizure focus. These more sensitive techniques can have a significant impact on the clinical practice by increasing the proportion of patients with identifiable "PET-positive" lesions to allow more patients to undergo transformative epilepsy surgery.

As indicated above, the disclosed subject matter includes improved algorithms based on compartment models with spillover and partial volume corrections. For example, the dynamic PET engine (and/or the ANN) can be configured to perform compartment modeling by optimizing a 3-compartment model developed in a rodent brain by solving the following equation:

$$C_T(t) =$$

$$\frac{K_1}{a_1 - a_2}[(k_3 + k_4 - a_1)e^{-a_1 t} + (a_2 - k_3 - k_4)e^{-a_2 t}] \otimes C_p(t) + BV \cdot C_p(t)$$

using non-linear regression, where $K_1$-$k_4$ are the kinetic parameters, $C_p$ is the blood input function, $\vartheta$ is the convolution operator, $a_1$, $a_2$ can be defined in terms of kinetic parameters as described and BV is the fraction of the blood volume in the tissue accounting for the SP contamination.

In one example, ten adult subjects with medically intractable focal epilepsy can be recruited for dynamic PET imaging with a clinical indication confirmed by ictal EEG videos and no localization from standard of care static PET imaging.

Accordingly, dynamic FDG PET imaging can be performed on these subjects. High resolution parametric maps of the temporal lobes using a compartment model will be computed by optimizing PBIF described above. Parametric $K_1$ and $k_3$ maps may also be computed by the dynamic PET engine. The parametric maps computed using the compartment model will be compared to a graphical Patlak model. Additionally, the quantitative parametric analysis can be compared to visual analysis by performing side to side comparisons on static PET (e.g., using last 15 minutes of dynamic data). The ANN methods described above may be optimized and tested in the seventeen subjects.

Figure 10:
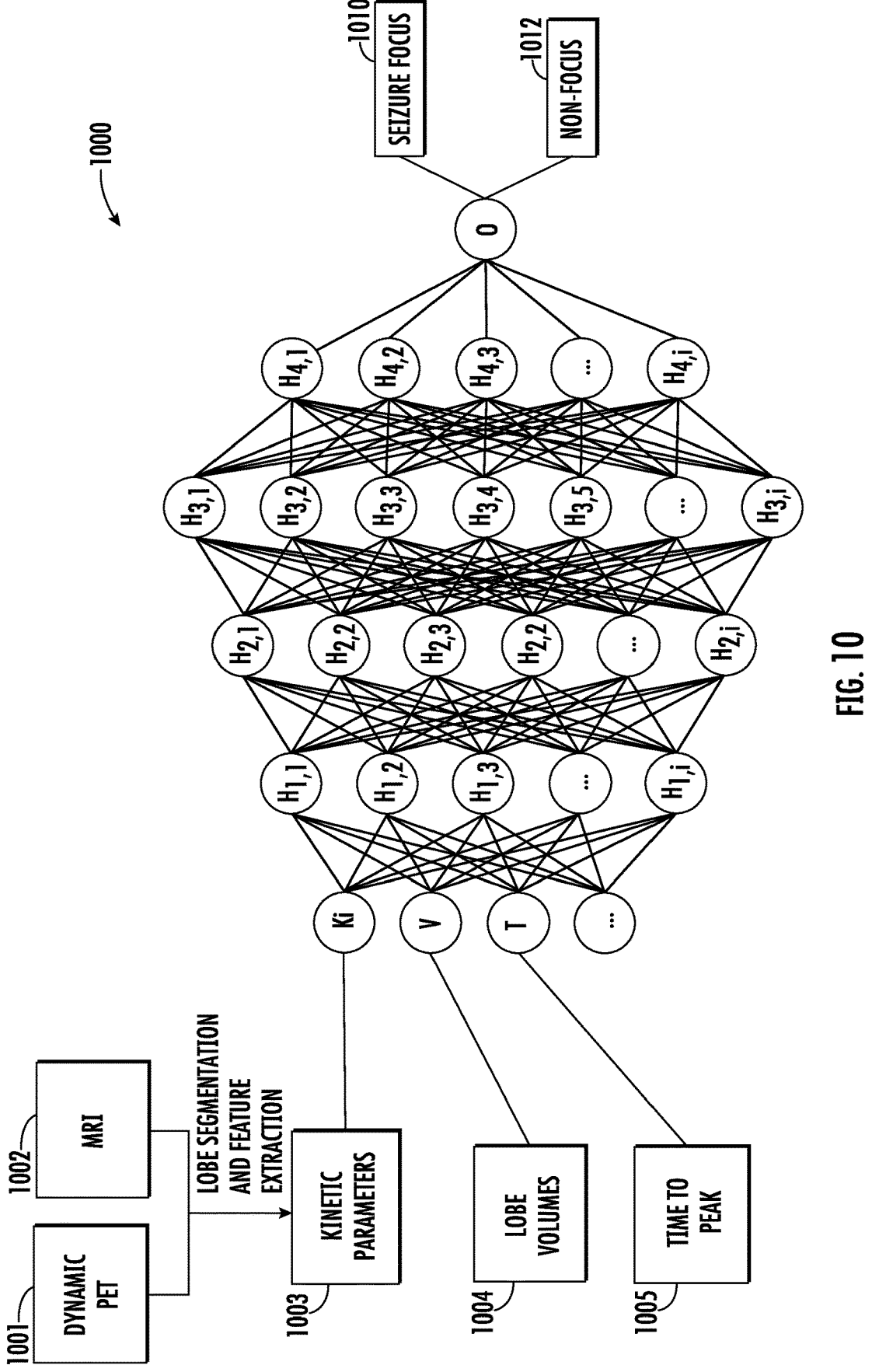
FIG. 10 is a diagram of a model framework of a deep forward artificial neural network configured for binary classification of subject brain lobe data according to an embodiment of the subject matter described herein.

In some embodiments, the dynamic PET ANN can be configured to utilize machine learning with clinical (MR) and radiomics features for improved hippocampal sclerosis detection in patients with temporal lobe epilepsy. For example, dynamic PET ANN may include a deep feed-forward neural network for binary classification of subject brain lobe data (e.g., see FIG. 10). Notably, FIG. 10 illustrates a deep feed-forward neural network 1000 (e.g., also ANN model 210 in FIG. 2) for binary classification of subject brain lobe data. Subject dynamic PET volume 1001 and MR volume 1002 can be segmented into individual lobes, and labelled as seizure focus or non-focus based on EEG video conclusions. Features for training (e.g., kinetic parameters 1003) may be extracted from the segmented volumes using compartment modeling (e.g., radiotracer uptake rate-K and time to peak 1005, T) and spatial measurements (e.g. regional volume V as represented by lobe volumes 1004) to create a robust feature set for input. The network may be initialized with leaky ReLU and a sigmoid output. The final model will be capable of determining the location of an epileptic seizure focus 1010 (and non-focus 1012) when fed in a subject's segmented brain volume.

In some embodiments, dynamic PET and MR images from a number of subjects, e.g., 17 subjects, can be segmented into the left and right sides of the five major lobes of the brain, each of which will contribute an individual sample to the model, yielding 170 total samples. Using results from EEG video, each lobe may receive binary labeling indicating whether or not it contains an epileptic focus. Features for neural network training will be extracted from the segmented lobe images themselves, or extracted from compartment modeling of regional kinetics. These two extraction techniques will yield a feature set of 10 metrics that are expected to relate to the disease state, including kinetic parameters from above and volumetric data from the segmented MR. The imbalance in class sizes, resulting from each subject mostly likely to contribute one seizure focus region and nine non-focal regions, will be accounted for using adjustments to the loss function and Synthetic Minority Oversampling Technique (SMOTE).

Deployment of the disclosed subject matter in this manner allows for the expectation that the high resolution parametric maps created using compartment models with SP and PV corrections will identify seizure foci in the temporal regions as opposed to extra temporal regions identified in the preliminary analysis performed using the graphical Patlak model (Table 1). Increasing sample size to what already imaged may result in more clinical findings. Additionally, increasing sample size may result in higher agreement with clinical standard (EEG findings). Increasing sample size may also result in identifying consistent regions of hypometabolism across subjects as opposed to varying number and regions intra subject.

It is expected that the disclosed initial neural network will be able to identify seizure foci at the lobe level in a subset of input data reserved for testing. It is further expected that these predictions will match the clinical standard for disease focus identification, and it is expected that this initial neural network will be easily adaptable to more data in order to eventually identify foci at a more clinically significant level, or to more accurate labelling data.

FIG. 9 is a flow chart illustrating an exemplary method for performing dynamic PET. In some embodiments, method 900 includes an algorithm and/or software process that is stored in memory and subsequently executed by one or more hardware processors of a computing platform. For example, method 900 can comprise a dynamic PET engine and/or a dynamic PET ANN described above (or a hardware based network element hosting and/or supporting dynamic PET engine and/or dynamic PET ANN). It will be appreciated that FIG. 9 is for illustrative purposes and that various entities, their locations, and/or their functions may be changed, altered, added, or removed. For example, some entities and/or functions may be combined into a single entity. In another example, an entity and/or function may be located at or implemented by two or more entities.

In step 902, a plurality of volumetric radioactive measurements of a target site (e.g., the brain) of a subject is collected over multiple scanning intervals. In some embodiments, a PET scanner device is utilized to acquire PET image data over a predefined time period comprising multiple scanning time intervals. For example, after a subject or patient is injected with an FDG radiotracer, the PET scanner device can be configured to collect volumetric radioactive measurement data (e.g., dynamic PET data) related to a target organ (e.g., the brain) of the subject over a series of time windows for a total duration of approximately 60 minutes. In some embodiments, the dynamic PET engine may be configured to instruct the data to be collected in a certain way, e.g., list mode acquisition which pertains to time stamped data as opposed to standard of care static non-list mode (e.g., non-time stamped) acquisition.

In step 904, a MR image of the target site is captured. In some embodiments, a MRI scanner device is used to capture an MR image of the target site/organ of the subject.

In step 906, motion correction to the volumetric radioactive measurement data to produce motion corrected data is performed. After the volumetric radioactive measurement data is obtained, the dynamic PET engine is configured to initiate an image pre-process stage by motion correcting the volumetric radioactive measurement data. Such processing helps to account for the movement of the subject during the collection of data in step 902. In some embodiments, the PET data is averaged across the first 14 frames to create a reference used to perform a rigid body transform across 38 frames.

In step 908, the MR image and motion corrected PET data are co-registered to produce a co-registered dynamic PET volume. In some embodiments, the average of all the motion corrected PET frames (e.g., in step 906) are resliced and co-registered (e.g., by the dynamic PET engine) with a T1 weighted MRI using a non-rigid transform to generate a transformation matrix that is used to generate a co-registered dynamic PET volume.

In step 910, a MCIF is applied to the co-registered dynamic PET volume to calibrate an uptake amount of the radioactive tracer in the target site. In some embodiments, the dynamic PET engine applies an MCIF to the voxels of the dynamic PET volume in order to calibrate the FDG uptake amount present in the target organ of the subject. Further, the dynamic PET engine can use the MCIF to generate whole brain parametric maps using the computed MCIF.

As indicated above, non-invasive identification of a clear seizure focus remains elusive in some patients. This may contribute to underutilization of surgery, even though guidelines recommend its use in those with medically-intractable focal epilepsy. Notably, 2-[18F] fluoro-2-deoxy-D-glucose positron emission tomography (FDG-PET) is an important component of the non-invasive presurgical localization because it measures neuronal metabolism rather than anatomy, as is done by MRI, or electrical activity as is done by EEG. When measured interictally, metabolically hypoactive regions revealed by decreased glucose uptake correspond to seizure foci. Focal hypometabolism predicts better outcomes when concordant with other data. When localizing information is discordant in the setting of normal MRI, FDG-PET aids in triage; for example, 63% of patients with normal MRI and discordant data had focal abnormalities on FDG-PET. Of those, 41% went on to have invasive monitoring or epilepsy surgery guided by FDG-PET.

However, traditional "static" FDG-PET (sFDG-PET) has limited sensitivity when it fails to indicate a clear hypometabolic focus. For example, in a study of presurgical tests, identification of seizure foci with sFDG-PET predicted one year seizure-remission with an odds ratio lower than other methods such as ictal single positron emission computed tomography, the presence of pre-operative auras, or concordance among presurgical procedures.

The disclosed subject matter includes a method of dynamic FDG-PET (dFDG-PET). Whereas sFDG-PET measures cerebral metabolism within a single time window of about 15 minutes, dFDG-PET maps radiation over a consecutive series of time windows for about 60 minutes. Analysis deconvolutes dynamic concentrations into a series of time-dependent "snapshots" that reveal rates of glucose uptake rather than final absolute uptake.

In some embodiments, the disclosed subject matter is based on studies that involve an intrasubject comparison of hypometabolic lesions revealed by dFDG-PET in those whose clinical sFDG-PET images were normal. For example, consented patients were enrolled if they were 1) age >17 years; 2) were reviewed in the University of Virginia's Epilepsy Surgery Conference and determined to have medically intractable focal epilepsy; 3) had normal sFDG-PET as reviewed in the epilepsy surgery review process. Patient exclusions included 1) the inability to obtain dFDG-PET without sedation; 2) diabetes mellitus; 3) psychogenic non-epileptic seizures or idiopathic generalized epilepsy; 4) weight >226 kg; and 4) implantation of a responsive neurostimulator.

In some instances, dFDG-PET studies were obtained on Siemens Biograph TOF mCT scanner. Dynamic acquisition consisted of an intravenous ~10 mCi tracer injection over 10 seconds with initiation of a 60-minute scan in list-mode format (e.g., see step 301 in FIG. 3). PET was preceded by a high resolution T1-weighted MPRAGE MRI (256 pixels× 256 pixels×192 slices) using a Siemens 3T scanner for co-registration (e.g., see step 302 in FIG. 3). Subsequent processing was performed with custom tools developed in Matlab (Mathworks Inc., Natick, MA). Image pre-processing started with motion correction for the 60-minute acquisition (e.g., see step 303 in FIG. 3). PET data (400 pixels× 400 pixels×111 slices×38-time frames) was averaged across the first 14 frames to create a reference used to perform a rigid body transform across the 38 frames. Although the example study utilized the first 14 frames to create a reference and 38 frames used to perform a rigid body transform, any other number of frames may be used without departing from the scope of the disclosed subject matter. The averages of all the motion-corrected PET frames were resliced and co-registered with T1-weighted MRI using non-rigid transform to generate a transformation matrix used, in turn, to generate a co-registered dynamic PET volume. Next, the MRI was co-registered with a high-resolution T1-weighted MRI template provided by the Montreal Neurological Institute (MNI) (e.g., see step 304 in FIG. 3) using a non-rigid transform, and a transformation matrix was generated. The total 164 regions of the Destrieux atlas, defined on the same MR brain template, were binned to generate 36 regions of interest (ROI) (18 regions/side). The above transformation matrix was inverted and applied to all ROIs to move them from the standard MNI template into the patient MRI (e.g., see step 305 in FIG. 3). All the above processes were performed using MRtrix functions. ROIs were then applied to the parametric maps (voxel-by-voxel maps) generated from dFDG-PET images.

Objective parametric PET maps were generated from model corrected blood input function (MCIF) corrected for partial volume (PV) averaging and spill-over (SP) contamination. As presented above, an IDIF from internal carotid artery in an early time frame (e.g., see step 306 in FIG. 3) for each patient was computed from the cohort average of 4 ROIs of the left internal carotid artery. These ROIs were applied to all the motion-corrected 38 PET frames to generate blood time activity curves ($PET_{IDIF}$). A model IDIF correcting the blood input for PV and tissue SP contamination can be written as $$\text{Model}_{IDIF,i} = \frac{\int_{t_b^i}^{t_e^i} [S_{Tb} C_T(t) + r_b C_a(t)] dt}{t_e^i - t_b^i}$$

in which $S_{Tb}$=SP contamination from the tissue to the blood at late time points $r_b$=blood recovery coefficient $t_b$ and $t_e$=beginning and end of a time frame.

$C_T(t)$, the model tissue, can be obtained by solving FDG transport differential equations from blood to tissue spaces. $C_a(t)$ is 7-parameter model blood for FDG transport as described. The above model IDIF was optimized using the following objective functions:

$$O_1(p) = \sum_{i=1}^{n} (\text{Model}_{IDIF,i} - PET_{IDIF,i})^2$$

$$O_2(p) = (\text{ModelPeak}_{IDIF} - PETPeak_{IDIF})^2$$

$$O(p) = O_1(p) + O_2(p)$$

ModelPeak was computed from the model equations for the IDIF ($\text{Model}_{IDIF}$) (equation 1). PETPeak values were derived from the dynamic PET blood images for each patient. Optimization of O(p) used non-linear regression analysis yielding the estimate of MCIF.

Each voxel of the dynamic data was then independently fed into a graphical Patlak model 11, together with the computed PBIF to compute whole brain parametric Ki and z-score maps (e.g., see step 307 in FIG. 3) applied to ROIs. The Patlak model performed a linear regression (starting at 10 minutes and beyond for which the image data were linear) where the slope provided a measure for the rate of FDG uptake at that voxel. Parallelization of multicore high-performance computers was used to compute whole-brain parametric maps for all patients. Data analysis was performed with (e.g., see step 307 in FIG. 3) z-score parametric mapping and (e.g., see step 308 in FIG. 3) segmented into regions of interest.

To monitor for seizures during acquisition, patients were monitored with video-EEG obtained with MRI-compatible scalp electrodes (Ives EEG Solutions, Manotick, Ontario, Canada).

Accordingly, the whole-brain voxel-level rate of FDG uptake (K) was computed from the motion-corrected, co-registered dFDG PET data for each patient subject. K maps for each patient were converted to voxel level z-score maps by normalizing to the whole brain mean and standard deviation within each patient. Average regional z-scores were computed for 36 regions of interest (18 regions/side). All regions with z-scores less than −1.65 standard deviations (SD), dictated by the default z-score threshold in MIM (https://www.mimsoftware.com/), were identified as hypometabolic compared to its contralateral side.

DISCUSSION

The disclosed subject matter is of particular use to focal epilepsy surgery candidates for whom sFDG-PET showed no abnormalities. Namely, dFDG-PET found focal regions of hypometabolism in all such cases. No patients undergoing trials related to the disclosed subject matter had adverse events. Related studies of dFDG-PET suggest that further research is merited to evaluate the specificity and sensitivity of dFDG-PET in larger cohorts to determine whether glucose uptake dynamics offer improved localization of epileptic foci over standard static PET techniques.

The disclosed subject matter builds on innovations around dFDG-PET and explored in rodent brains and models of movement disorders, human ambulatory metabolic studies, and brain cancer. A critical and innovative step is the development of the disclosed blood input function that calibrates the calculation of FDG uptake. In animals, direct measurement through arterial blood or in non-invasive estimates that derive blood input function from images of left ventricular blood are possible. In human brain imaging, however, the requirement for non-invasive estimation within a limited image field led to the disclosed technique of estimations via images of the internal carotid arteries with model based partial volume corrections. Other developments include the "turn-key" application of automated movement-correction software required over the one hour scan time, a process in the past that was largely performed manually.

One goal of disclosed subject matter is to provide initial data to drive further work in validation of dFDG-PET. The disclosed subject matter suggests that dFDG-PET may indicate focal regions of hypometabolism in epilepsy surgery subjects whose standard static FDG-PET was unhelpful and whose non-invasive, "phase 1" evaluations did not disclose clear or single surgical targets. The plan is to design trials that will calculate specificity and sensitivity of dFDG-PET to the "ground truth" of seizure freedom following epilepsy surgery. It is noted that one patient who underwent successful surgery (patient 4), dFDG-PET predicted the surgical target. In contrast, for the one patient who had prior unsuccessful surgery (patient 7), dFDG-PET indicated a different surgical target than the one undertaken (e.g., subsequent intracranial monitoring disclosed probable multifocal foci).

Notably, dFDG-PET may offer additional sensitivity over sFDG-PET to reveal epileptic networks since it captures the kinetics of glucose wash-in, metabolism, and wash-out from the point of injection. An advantage of the disclosed technique is that it is potentially transportable to any facility with an appropriate PET scanner, a possible transformative method to allow current hardware to improve non-invasive localization. Further software development is needed to create a complete imaging package that can be implemented among different centers.

In conclusion, the disclosed subject matter has demonstrated that dFDG-PET can offer non-invasive localization of potential epileptic foci. With further validation, dFDG-PET may offer more patients the advantages of presurgical localization and possibly convert those who may be non-candidates into candidates for transformative epilepsy surgery.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for performing dynamic positron emission tomography (PET), the method comprising:
   collecting volumetric radioactive measurement data associated with an administered radioactive tracer present in a target site of a subject over multiple scanning intervals;
   capturing a magnetic resonance image of the target site;

performing a motion correction process to the volumetric radioactive measurement data to produce motion corrected PET data;

co-registering the magnetic resonance image and motion corrected data to generate a co-registered dynamic PET volume; and applying a model corrected input function (MCIF) to the co-registered dynamic PET volume to calibrate an uptake amount of the radioactive tracer in the target site.

2. The method of claim 1 wherein collecting the volumetric radioactive measurement data over the multiple scanning intervals comprises continuously collecting a plurality of volumetric radioactive measurements at the multiple scanning intervals over a predefined time period.

3. The method of claim 1 wherein prior to the collecting step, the subject is injected with the radioactive tracer.

4. The method of claim 1 wherein the volumetric radioactive measurement data indicates a changing of concentrations of the radioactive tracer per each of the multiple scanning intervals.

5. The method of claim 1 wherein the MCIF is determined and applied automatically via an artificial neural network (ANN).

6. The method of claim 1 wherein the MCIF is used to generate objective parametric PET maps of the target site.

7. The method of claim 1 wherein a plurality of blood time activity curves generated from a plurality of frames of the co-registered dynamic PET volume is used to derive the MCIF.

8. A system for performing dynamic positron emission tomography (PET), the system comprising:

a PET scanner device configured for configured for collecting volumetric radioactive measurement data associated with an administered radioactive tracer present in a target site of a subject over multiple scanning intervals;

a magnetic resonance imaging scanner device configured for capturing a magnetic resonance image of the target site;

a dynamic PET platform comprising:

at least one processor;

a memory element; and a dynamic PET engine stored in the memory element and when executed by the at least one processor is configured for receiving the magnetic resonance image and the volumetric radioactive measurement data, performing a motion correction process to the volumetric radioactive measurement data to produce motion corrected PET data, co-registering the magnetic resonance image and motion corrected data to generate a co-registered dynamic PET volume; and applying a model corrected input function (MCIF) to the co-registered dynamic PET volume to calibrate an uptake amount of the radioactive tracer in the target site.

9. The system of claim 8 wherein collecting the volumetric radioactive measurement data over the multiple scanning intervals comprises continuously collecting a plurality of volumetric radioactive measurements at the multiple scanning intervals over a predefined time period.

10. The system of claim 8 wherein the subject is injected with the radioactive tracer prior to the collection of the volumetric radioactive measurement data.

11. The system of claim 8 wherein the volumetric radioactive measurement data indicates a changing of concentrations of the radioactive tracer per each of the multiple scanning intervals.

12. The system of claim 8 wherein the MCIF is determined and applied automatically via an artificial neural network (ANN).

13. The system of claim 8 wherein the MCIF is used to generate objective parametric PET maps of the target site.

14. The system of claim 8 wherein a plurality of blood time activity curves generated from a plurality of frames of the co-registered dynamic PET volume is used to derive the MCIF.

15. One or more non-transitory computer readable media having stored thereon executable instructions that when executed by a processor of a computer cause the computer to perform steps comprising:

collecting volumetric radioactive measurement data associated with an administered radioactive tracer present in a target site of a subject over multiple scanning intervals;

capturing a magnetic resonance image of the target site;

performing a motion correction process to the volumetric radioactive measurement data to produce motion corrected PET data;

co-registering the magnetic resonance image and motion corrected data to generate a co-registered dynamic PET volume; and applying a model corrected input function (MCIF) to the co-registered dynamic PET volume to calibrate an uptake amount of the radioactive tracer in the target site.

16. The one or more non-transitory computer readable media of claim 15 wherein collecting the volumetric radioactive measurement data over the multiple scanning intervals comprises continuously collecting a plurality of volumetric radioactive measurements at the multiple scanning intervals over a predefined time period.

17. The one or more non-transitory computer readable media of claim 15 wherein prior to the collecting step, the subject is injected with the radioactive tracer.

18. The one or more non-transitory computer readable media of claim 15 wherein the volumetric radioactive measurement data indicates a changing of concentrations of the radioactive tracer per each of the multiple scanning intervals.

19. The one or more non-transitory computer readable media of claim 15 wherein the MCIF is determined and applied automatically via an artificial neural network (ANN).

20. The one or more non-transitory computer readable media of claim 15 wherein the MCIF is used to generate objective parametric PET maps of the target site.

* * * * *